United States Patent [19]

Smith

[11] 4,159,997

[45] Jul. 3, 1979

[54] 2-DECARBOXY-2-HYDROXYMETHYL-6-HYDROXY-PGE$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 918,525

[22] Filed: Jun. 23, 1978

Related U.S. Application Data

[63] Continuation-in-part of Ser. No. 812,794, Jul. 5, 1977, Pat. No. 4,131,738.

[51] Int. Cl.$^2$ .............................................. C07C 177/00
[52] U.S. Cl. ................................................ 260/586 R
[58] Field of Search ..................................... 260/586 R

[56]  References Cited

U.S. PATENT DOCUMENTS

| | | | |
|---|---|---|---|
| 3,950,363 | 4/1976 | Bundy | 260/347.3 |
| 4,013,695 | 3/1977 | Lin | 260/410.9 R |
| 4,060,534 | 11/1977 | Bundy | 260/408 |

*Primary Examiner*—Gerald A. Schwartz
*Attorney, Agent, or Firm*—Robert A. Armitage

[57] ABSTRACT

The present invention provides 2-decarboxy-2-hydroxymethyl-6-hydroxy-PGE$_1$ compounds which are useful pharmacological agents. These agents are useful as prostacyclin-like drugs.

34 Claims, No Drawings

2-DECARBOXY-2-HYDROXYMETHYL-6-HYDROXY-PGE₁ COMPOUNDS

CROSS REFERENCE TO RELATED APPLICATION

This application is a continuation-in-part of Ser. No. 812,794, filed July 5, 1977, now pending issuance as a United States patent.

The present invention relates to 2-decarboxy-2-hydroxymethyl-6-hydroxy-PGE₁ compounds, the preparation and use of which are described in United States Ser. No. 812,794, filed July 5, 1977, now pending issuance as a United States patent.

The essential material constituting a disclosure of the instant invention is incorporated by reference here from United States Ser. No. 812,794, filed July 5, 1977.

I claim:

1. A prostacyclin analog of the formula

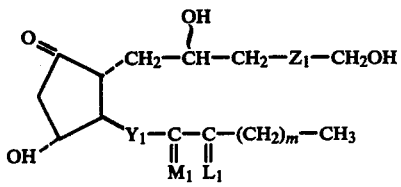

wherein $Z_1$ is
(1) $-(CH_2)_g-CH_2-CH_2-$,
(2) $-(CH_2)_g-CH_2-CF_2-$, or
(3) trans-$(CH_2)_g-CH=CH-$,
 wherein g is the integer one, 2, or 3;
wherein $Y_1$ is
(1) trans-CH=CH—,
(2) cis-CH=CH—,
(3) —CH₂CH₂—,
(4) trans-CH=C(Hal)—, or
(5) —C≡C—,
 wherein Hal is chloro or bromo;
wherein $M_1$ is

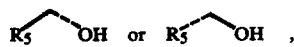

wherein $R_5$ is hydrogen or alkyl with one to 4 carbon atoms, inclusive;
wherein $L_1$ is

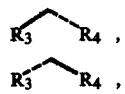

or a mixture of

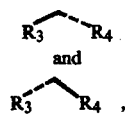

wherein $R_3$ and $R_4$ are hydrogen, methyl, or fluoro, being the same or different, with the proviso that one of $R_3$ and $R_4$ is fluoro only when the other is hydrogen or fluoro; and
wherein m is the integer one to 5, inclusive.

2. A prostacyclin analog according to claim 1, wherein ~OH is beta.
3. 2-Decarboxy-2-hydroxymethyl-6β-hydroxy-PGE₁, a prostacyclin analog according to claim 2.
4. A prostacyclin analog according to claim 1 wherein ~OH is alpha.
5. 2-Decarboxy-2-hydroxymethyl-6α-hydroxy-PGE₁, a prostacyclin analog according to claim 4.
6. 2-Decarboxy-2-hydroxymethyl-6α-hydroxy-15-methyl-PGE₁, a prostacyclin analog according to claim 4.
7. 2-Decarboxy-2-hydroxymethyl-6α-hydroxy-16,16-dimethyl-PGE₁, a prostacyclin analog according to claim 4.
8. 2-Decarboxy-2-hydroxymethyl-6α-hydroxy-16,16-difluoro-PGE₁, a prostacyclin analog according to claim 4.
9. A prostacyclin analog according to claim 1 wherein ~OH is a mixture of α-OH and β-OH.
10. A prostacyclin analog according to claim 9 wherein $Y_1$ is cis-CH=CH—.
11. 2-Decarboxy-2-hydroxymethyl-6-hydroxy-cis-13-PGE₁, a prostacyclin analog according to claim 10.
12. A prostacyclin analog according to claim 9 wherein $Y_1$ is —C≡C—.
13. 2-Decarboxy-2-hydroxymethyl-6-hydroxy-13,14-didehydro-PGE₁, a prostacyclin analog according to claim 12.
14. A prostacyclin analog according to claim 9 wherein $Y_1$ is trans-CH=C(Hal)—.
15. 2-Decarboxy-2-hydroxymethyl-6-hydroxy-14-chloro-PGE₁, a prostacyclin analog according to claim 14.
16. A prostacyclin analog according to claim 9 wherein $Y_1$ is —CH₂CH₂—.
17. 2-Decarboxy-2-hydroxymethyl-6-hydroxy-13,14-dihydro-PGE₁, a prostacyclin analog according to claim 16.
18. A prostacyclin analog according to claim 9 wherein $Y_1$ is trans-CH=CH—.
19. A prostacyclin analog according to claim 18 wherein $Z_1$ is —(CH₂)$_g$—CH₂—CF₂—.
20. 2-Decarboxy-2-hydroxymethyl-2,2-difluoro-6-hydroxy-15-methyl-PGE₁, a prostacyclin analog according to claim 19.
21. A prostacyclin analog according to claim 18 wherein $Z_1$ is trans-(CH₂)$_g$—CH=CH—.
22. 2-Decarboxy-2-hydroxymethyl-trans-2,3-didehydro-6-hydroxy-PGE₁, a prostacyclin analog according to claim 21.
23. A prostacyclin analog according to claim 18 wherein $Z_1$ is —(CH₂)$_g$—CH₂—CH₂—.
24. A prostacyclin analog according to claim 23 wherein g is one.
25. A prostacyclin analog according to claim 24 wherein m is 3.
26. A prostacyclin analog according to claim 25 wherein $R_5$ is methyl.
27. 2-Decarboxy-2-hydroxymethyl-6-hydroxy-15-methyl-PGE₁, a prostacyclin analog according to claim 26.
28. A prostacyclin analog according to claim 25 wherein $R_5$ is hydrogen.
29. A prostacyclin analog according to claim 28 wherein at least one of $R_3$ and $R_4$ is fluoro.
30. 2-Decarboxy-2-hydroxymethyl-6-hydroxy-16,16-difluoro-PGE₁, a prostacyclin analog according to claim 29.

31. A prostacyclin analog according to claim 28 wherein at least one of $R_3$ and $R_4$ is methyl.

32. 2-Decarboxy-2-hydroxymethyl-6-hydroxy-16,16-dimethyl-$PGE_1$, a prostacyclin analog according to claim 31.

33. A prostacyclin analog according to claim 28 wherein $R_3$ and $R_4$ are both hydrogen.

34. 2-Decarboxy-2-hydroxymethyl-6-hydroxy-$PGE_1$, a prostacyclin analog according to claim 33.

UNITED STATES PATENT OFFICE
CERTIFICATE OF CORRECTION

Patent No. 4,159,997                        Dated 3 July 1979

Inventor(s) Herman W. Smith

It is certified that error appears in the above-identified patent and that said Letters Patent are hereby corrected as shown below:

Column 1, lines 8-9, "now pending issuance as a United States patent." should read -- now issued as U.S. Patent 4,131,738. --;
Column 1, lines 13-14, "now pending issuance as a United States patent." should read -- now issued as U.S. Patent 4,131,738 on December 26, 1978. --;
Column 1, line 17, "United States Ser. No. 812,794, filed July 5, 1977." should read -- U.S. Patent 4,131,738. --.

*Signed and Sealed this*

*Twenty-seventh* Day of *November 1979*

[SEAL]

Attest:

RUTH C. MASON
*Attesting Officer*

LUTRELLE F. PARKER
*Acting Commissioner of Patents and Trademarks*